United States Patent
Murphy et al.

(10) Patent No.: US 6,508,826 B2
(45) Date of Patent: Jan. 21, 2003

(54) CANNULA WITH FLOW DIVERSION MECHANISM AND METHODS OF USE

(75) Inventors: Richard O. Murphy, Sunnyvale, CA (US); Richard S Lilly, San Jose, CA (US)

(73) Assignee: EMBOL-X, Inc., Mountain View, CA (US)

( * ) Notice: Subject to any disclaimer, the term of this patent is extended or adjusted under 35 U.S.C. 154(b) by 55 days.

(21) Appl. No.: 09/846,309

(22) Filed: Apr. 30, 2001

(65) Prior Publication Data

US 2002/0161391 A1 Oct. 31, 2002

(51) Int. Cl.⁷ .............................................. A61M 29/00
(52) U.S. Cl. ...................................... 606/200; 606/198
(58) Field of Search ................................ 606/200, 198, 606/195, 191, 194, 192, 108; 604/96.01, 104; 128/898

(56) References Cited

U.S. PATENT DOCUMENTS

| | | | |
|---|---|---|---|
| 5,846,260 A | 12/1998 | Maahs ......................... | 606/200 |
| 5,989,281 A | 11/1999 | Barbut et al. ................ | 606/200 |
| 6,007,557 A | 12/1999 | Ambrisco et al. ........... | 606/200 |
| 6,068,621 A * | 5/2000 | Balceta et al. ........... | 606/200 X |
| 6,090,097 A | 7/2000 | Barbut et al. ................ | 604/511 |
| 6,129,713 A * | 10/2000 | Mangosong et al. ........ | 604/264 |
| 6,165,200 A * | 12/2000 | Tsugita et al. .............. | 606/200 |
| 6,231,544 B1 * | 5/2001 | Tsugita et al. .............. | 604/104 |
| 6,235,044 B1 * | 5/2001 | Root et al. ................... | 606/200 |
| 6,290,710 B1 * | 9/2001 | Cryer et al. ................. | 606/200 |
| 6,364,896 B1 * | 4/2002 | Addis .......................... | 606/200 |
| 6,371,969 B1 * | 4/2002 | Tsugita et al. .............. | 606/200 |

* cited by examiner

*Primary Examiner*—Gloria M. Hale
(74) *Attorney, Agent, or Firm*—O'Melveny & Myers LLP

(57) ABSTRACT

A cannula is described that includes a diverter mechanism in the form of a blast plate deployable from within the lumen of the cannula and retractable from the lumen of the cannula. The blast plate may take the form of a planar surface, a curved surface, a membrane mounted on a wire ring, or a conical sleeve, or any other suitable shape. In use, the cannula is inserted in a vessel, the blast plate is deployed in the lumen of the cannula beyond the distal end of the cannula, and blood flow is passed through the cannula and against the blast plate. Alternative devices and methods are also described.

20 Claims, 7 Drawing Sheets

CANNULA WITH FLOW DIVERSION MECHANISM AND METHODS OF USE

FIELD OF THE INVENTION

The present invention relates generally to medical devices useful for cannulation of a vascular tissue, such as the aorta, and for protecting against distal embolization during cardiovascular procedures. More particularly, the devices minimize plaque dislodgement and damage to a vessel wall during delivery of blood to the vessel.

BACKGROUND OF THE INVENTION

Aortic cannulation is commonly employed during various conventional or minimally invasive surgeries, such as coronary artery bypass grafting, heart valve repair or replacement, septal defect repair, pulmonary thrombectomy, atherectomy, aneurysm repair, aortic dissection repair, and correction of congenital defects, to establish cardiopulmonary bypass. After circulatory isolation of the coronary blood flow from the peripheral vascular system is established, a cannula is usually inserted in the ascending aorta to deliver oxygenated blood from a bypass-oxygenator to maintain blood flow to the peripheral organs, e.g., the brain and kidneys. It is well recognized that one of the complications associated with cardiovascular procedures is the dislodgement of embolic materials generated during manipulation of the aorta or the heart, thereby causing occlusion of the vessels downstream from the aorta causing ischemia or infarct of the organs, e.g., stroke. To minimize embolic complication, an arterial filter is often temporarily deployed in the aorta distal to the aortic cannula to capture embolic debris.

However, when oxygenated blood is delivered to the aortic cannula through the bypass-oxygenator, blood exits the cannula with a very high velocity, similar to a jet-like profile. When this jet is directed toward the aortic wall, it may damage the aorta causing aortic dissection or aneurysm. Furthermore, the jet may dislodge plaque on the aortic wall, causing distal embolization and peripheral organ infarction. When oxygenated blood is allowed to flow into a filter, the jet may cause turbulent flow in the filter, thereby washing out the emboli caught in the filter. As a result of the swirling action by the jet, the emboli may escape around the edges of the filter to cause distal embolization and result in damage to peripheral organs, or may travel upstream to reach a coronary artery and cause myocardial infarction.

New devices and methods are thus needed in aortic cannulation to minimize embolic dislodgement and vascular wall damage due to delivery of oxygenated blood to the aorta during cardiovascular surgeries.

SUMMARY OF THE INVENTION

The invention provides devices and methods for reducing the jet-like profile of blood delivered through a cannula and the swirling of the blood within a filter. It will be understood that, although the present invention is most useful in aortic cannulation during cardiovascular surgeries, the devices and methods can be used in any surgeries where delivery of fluid or blood through a cannula can potentially damage the body tissue.

In a first embodiment, the cannula is an elongate tubular member having a proximal end, a distal end, and a lumen therebetween. A blast plate deployable from within the lumen of the elongate tubular member is provided. The blast plate is retractable into the lumen of the elongate tubular member after use. In certain cases, the cannula is angled at its distal end, generally at a 90° angle to the axis of the lumen at a proximal end. In other cases, the cannula will further include a filter deployable from the distal end of the cannula. The filter may be mounted on the distal end of the cannula, or the filter can be mounted on a separately insertable member, such as a guidewire. In other cases, the cannula has more than one lumen extending from its proximal to its distal end. In still other cases, the cannula further comprises an occlusion member such as a balloon occluder, deployable from the distal end of the cannula. As with the filter, the occluder can be mounted on the cannula, or provided on a separately insertable member, such as an occlusion catheter.

The blast plate typically comprises a generally flat or curved surface, and may comprise a membrane mounted on a flexible wire ring. The membrane generally comprises a semi-permeable material. In certain cases the member is a mesh material. In still other cases, the membrane is made of an impermeable material. While in certain cases the blast plate is formed in the shape of a planar surface defined by a wire ring, in other cases the blast plate is a cone-shaped sleeve. The sleeve can be made of an elastomeric material. The blast plate may also take the form of a substantially flat surface mounted at the distal end of a flexible or an inflexible elongate member. For example, the blast plate may be fixed to the end of a wire. The blast plate will be angled relative to the elongate member, and the angle may be selected from a 45° angle, a 50° angle, a 55° angle, a 60° angle, a 65° angle, a 70° angle, a 75° angle, an 80° angle, an 85° angle, or a 90° angle.

In use, the surgeon inserts the cannula into a body cavity, e.g., a blood vessel. It will be understood that the cannula may comprise a standard commercially available cannula, or any of the novel cannula described herein. The surgeon will then advance a blast plate or dispersion mechanism through the lumen of the cannula and beyond the distal end of the cannula. The surgeon then flows a stream of fluid, e.g., blood, through the lumen of the cannula. The blood flow hits the blast plate, and the blood stream is diffused and dispersed by the blast plate without jetting against the wall of the aorta. After the infusion procedure is complete, the surgeon retracts the blast plate into the lumen of the cannula.

It will be understood that the methods of use have particular application where the body cavity is a blood vessel, where the blood vessel is an artery, and where the artery is the aorta. It will further be understood that there are several advantages to using the diffusion-diversion devices and methods described herein. For example, by dispersing the stream of blood flow, the devices and methods (1) avoid "sand blasting" embolic debris from the lumen of the vessel, (2) avoid the swirling of blood that may carry embolic debris upstream during CABG to the coronary arteries, where myocardial ischemia can occur, (3) avoid turbulence that can force embolic debris around the periphery of a deployed filter to cause distal embolization which can results in stroke, renal failure, or other organ damage.

DETAILED DESCRIPTION

Figure 1A:
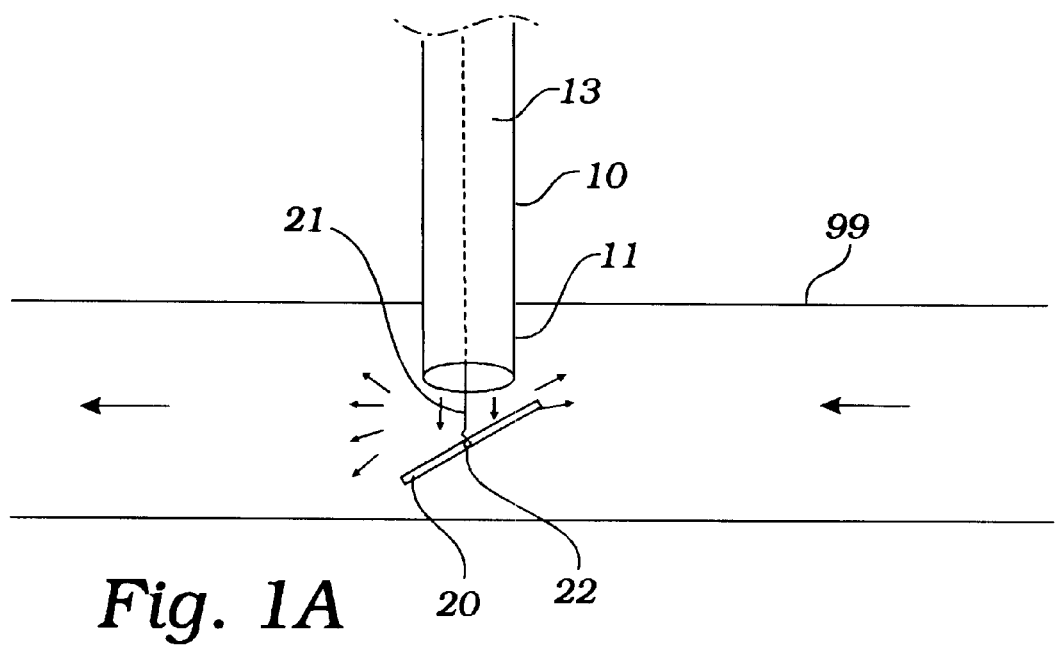
FIG. 1A depicts a cannula having a blast plate deployed within an artery.
Figure 1B:
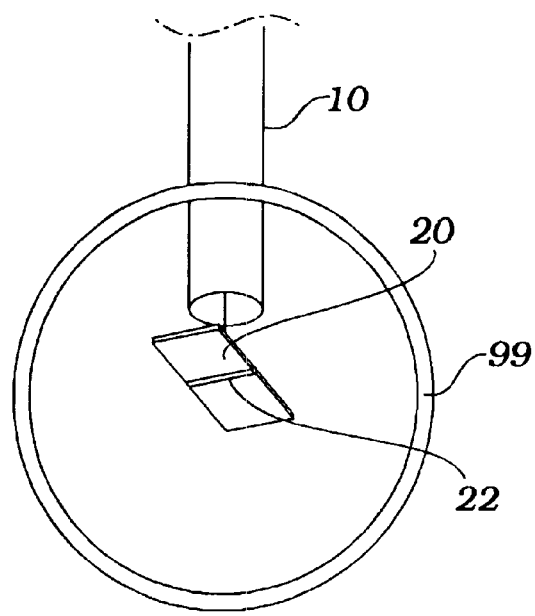
FIG. 1B depicts an end view of the artery and cannula of FIG. 1A.

A first cannula with flow diverter is depicted in FIG. 1A. Cannula 10 having distal end 11 is deployed through an incision in vessel 99, in certain cases the aorta. Blast plate 20 is fixed to elongate wire 21 at bond 22. Blast plate 20 is deployed through lumen 13 of cannula 10. Blood flow exits cannula 10, impacts blast plate 20, and is scattered as shown by the arrows surrounding blast plate 20. FIG. 1B depicts an end view of the diverter and cannula of FIG. 1B. As shown in FIG. 1A, blast plate 20 is not necessarily flat but can take on a curvilinear configuration.

Figure 1C:
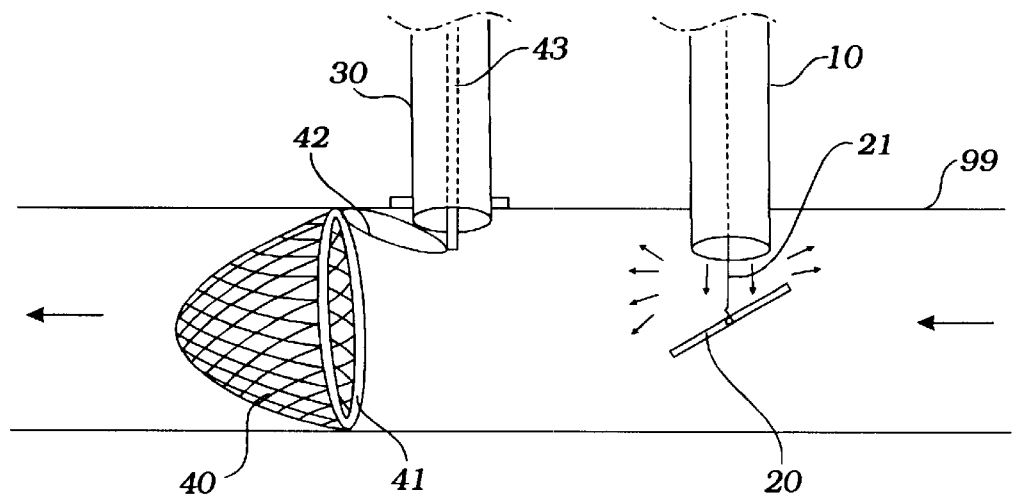
FIG. 1C depicts a cannula with blast plate deployed within an artery, and a separately deployed filter through a second cannula.

FIG. 1C shows a cannula and diverter deployed within vessel 99, and a separate filter cannula. Filter cannula 30 carries separately insertable elongate member 43 having expansion frame 41 and mesh 40 disposed at a distal end of elongate member 43. Expansion frame 41 is attached to elongate member 43 through active anchor wire 42. It will be understood that anchor wire 42 allows expansion frame 41 to expand to fill the lumen of vessel 99. Mesh 40 is attached at an edge to expansion frame 41. In other devices, expansion frame 41 may be directly connected to elongate member 43. In this manner, the filter mechanism is separately insertable through cannula 30, which is introduced as a separate stick on vessel 99.

Figure 1D:
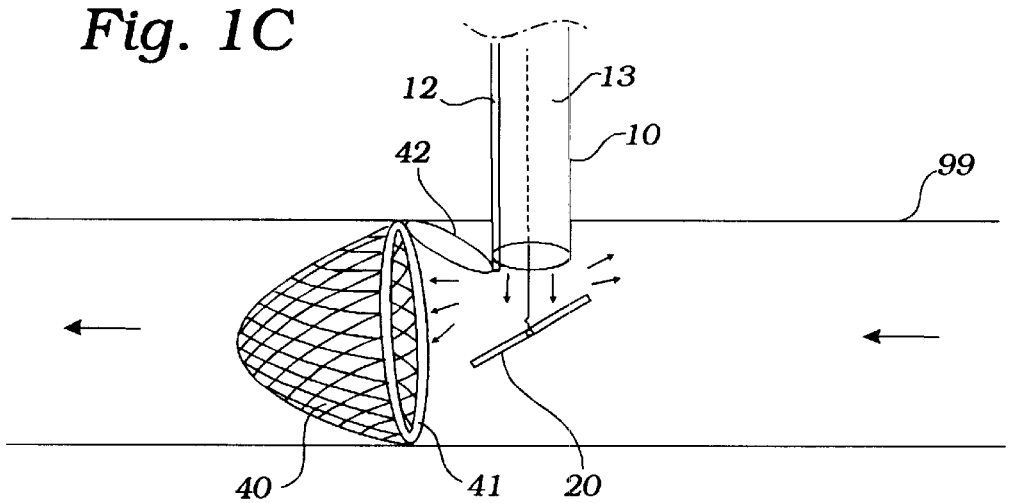
FIG. 1D depicts a cannula having a filter and a blast plate deployed through separate lumens of the cannula.
Figure 1E:
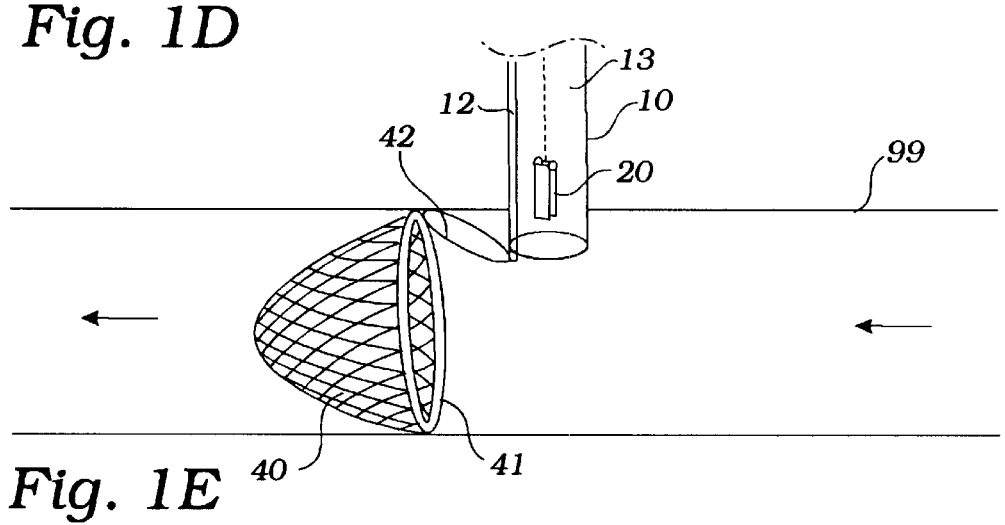
FIG. 1E depicts removal of the blast plate of FIG. 1D.

FIG. 1D depicts cannula 10 having first lumen 13 and second lumen 12. First lumen 13 is adapted for insertion of diverter mechanism 20. Second lumen 12 is adapted to receive and pass a separately insertable filter disposed at the distal end of an elongate member. FIG. 1E depicts blast plate 20 being withdrawn through lumen 13 of cannula 10.

In certain alternative embodiments, diverter 20 or alternately the filter/diverter may be stored in lumen 13 through which blood flows, so that the onset of flow causes diverter mechanism 20 and/or the filter to move distally and deploy once ejected from the tip of the cannula. The mechanism may be tethered to the cannula and may be removed with the cannula or withdrawn back into lumen 13 using a wire.

Figure 2A:
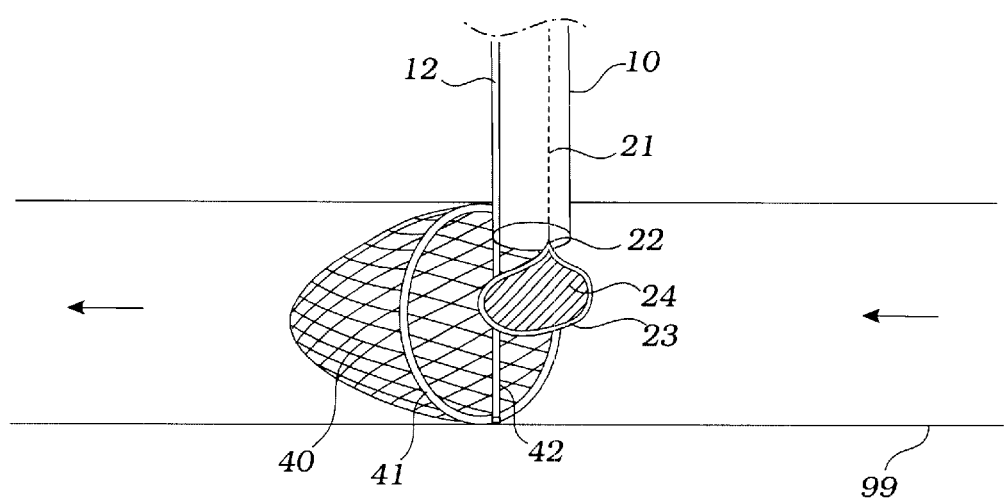
FIG. 2A depicts a blast plate comprising a membrane mounted on a flexible wire ring.
Figure 2B:
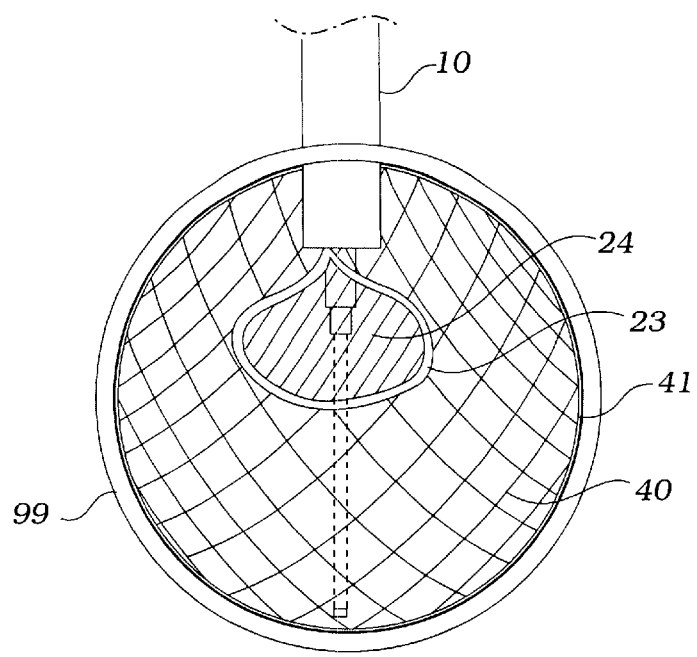
FIG. 2B depicts an end view of the artery and cannula of FIG. 2A.

FIG. 2A shows an alternative construction of a diverter mechanism and filter protection device. The diverter comprises wire ring 23 fixed to elongate member 21 at bond 22. An impermeable or semi-permeable material 24 covers wire ring 23 and acts as a blast plate for existing blood flow. Filter 40 includes expansion frame 41 and cantilever 42. The reader is referred to Ambrisco et al., U.S. Pat. No. 6,007,557, incorporated as if set forth in its entirety herein, for details on the design of a cantilever-based expansion frame. FIG. 2B depicts an end view of a membrane blast plate as shown in FIG. 2A.

Figure 3A:
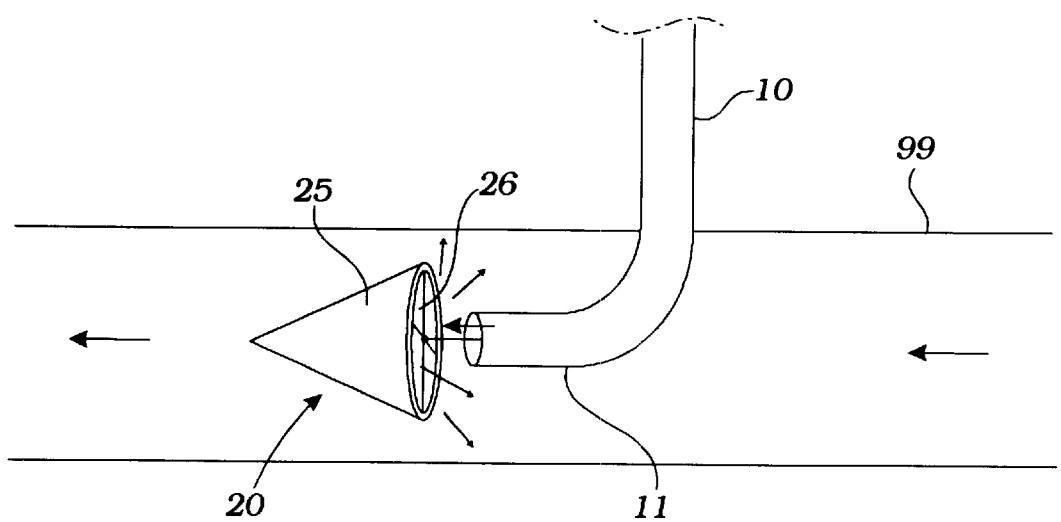
FIG. 3A depicts a diverter that comprises a cone-shaped sleeve.
Figure 3B:
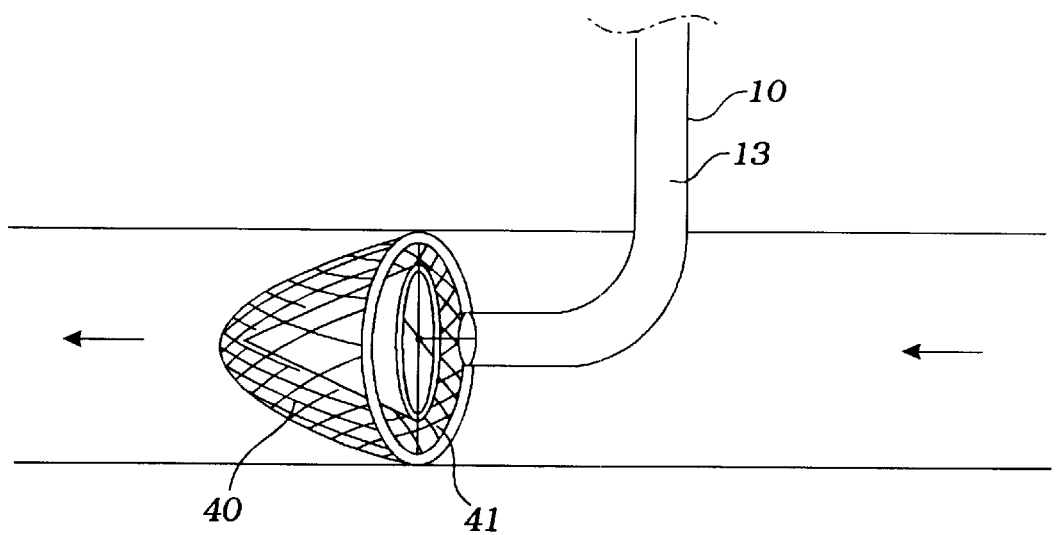
FIG. 3B depicts the diverter of FIG. 3A deployed within a filter.
Figure 3C:
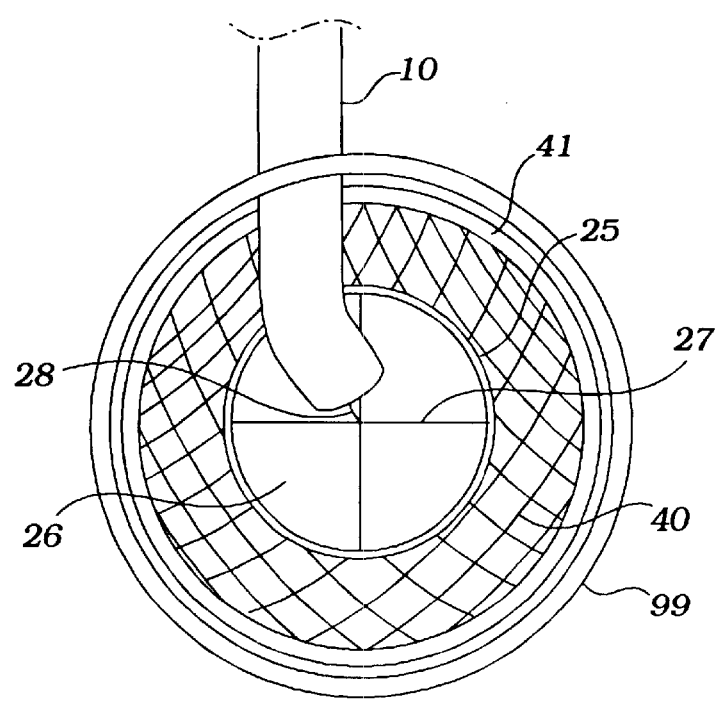
FIG. 3C depicts an end view of the diverter and filter of FIG. 3B.
Figure 3D:
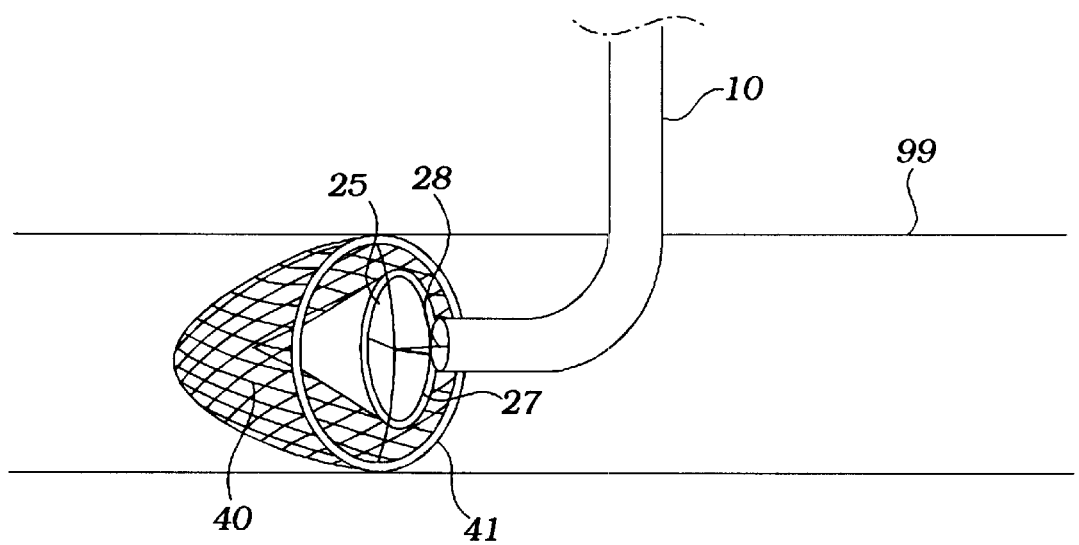
FIG. 3D depicts an oblique view of the diverter and filter of FIG. 3B.

FIG. 3A shows cannula 10 having angled distal end 11 disposed within vessel 99. Diverter 20 takes the form of cone-shaped sleeve 25 formed of an impermeable or semi-permeable material. Sleeve 25 is open at proximal end 26 for receiving blood flow from arterial return cannula 10. Sleeve 25 disperses the jet stream of blood as shown by the arrows surrounding sleeve 25. FIG. 3B shows sleeve 25 used with filter 40 mounted on expansion frame 41. FIG. 3C depicts an end view of the filter with the cone-shaped sleeve of FIG. 3B. Sleeve 25 is connected to elongate member 28 by struts 27. Elongate member 28 and sleeve 25 are separately insertable through cannula 10. Filter 40 and expansion frame 41 may be separately insertable or may be mounted on the distal region of cannula 10. FIG. 3D shows an oblique view of the cannula, cone-shaped diverter sleeve, and filter of FIG. 3B.

Figure 4A:
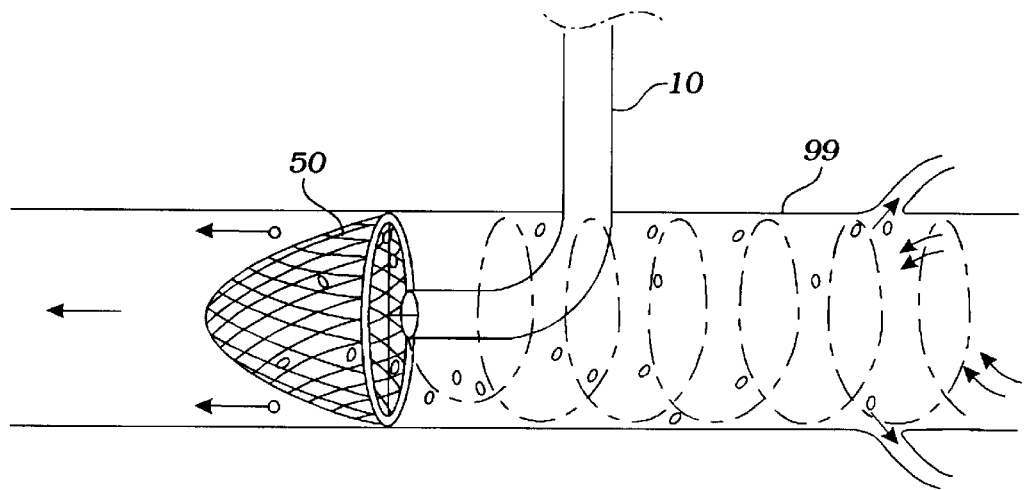
FIG. 4A depicts a standard cannula and filter without a diverter.
Figure 4B:
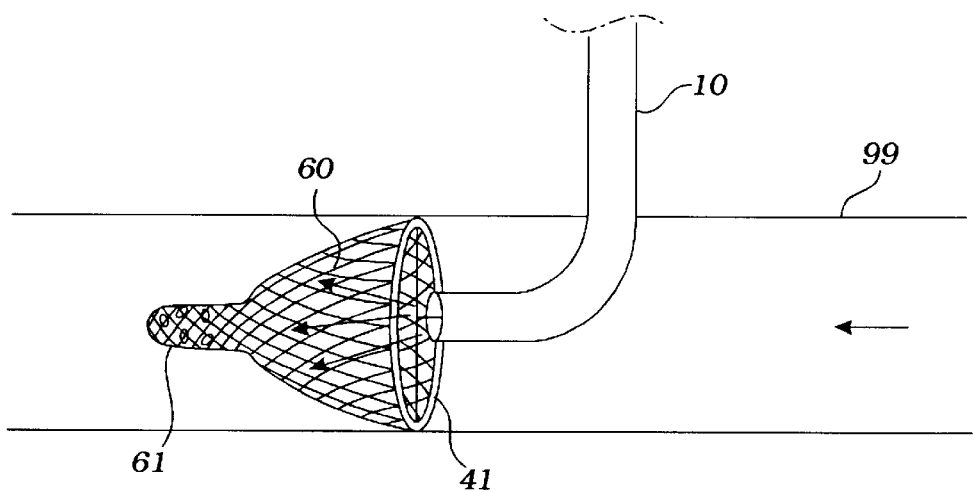
FIG. 4B depicts a filter and cannula having a windsock embolic trap incorporated in the filter.

FIG. 4A depicts standard cannula 10 and filter 50, without diverter capabilities. Unscattered blood flow from cannula 10 creates turbulence within filter 50 that may cause emboli to escape downstream, and may carry other emboli upstream where they can become lodged in the coronary arteries, resulting in myocardial ischemia or infarct. FIG. 4B shows a filter construction that traps emboli to prevent movement within turbulent blood flow. Expansion frame 41 is attached to filter mesh 60 that includes reservoir tip 61 (in the shape of a windsock) for retaining captured emboli. This design will immobilize emboli and minimize the opportunity for proximal and distal embolization.

Figure 4C:
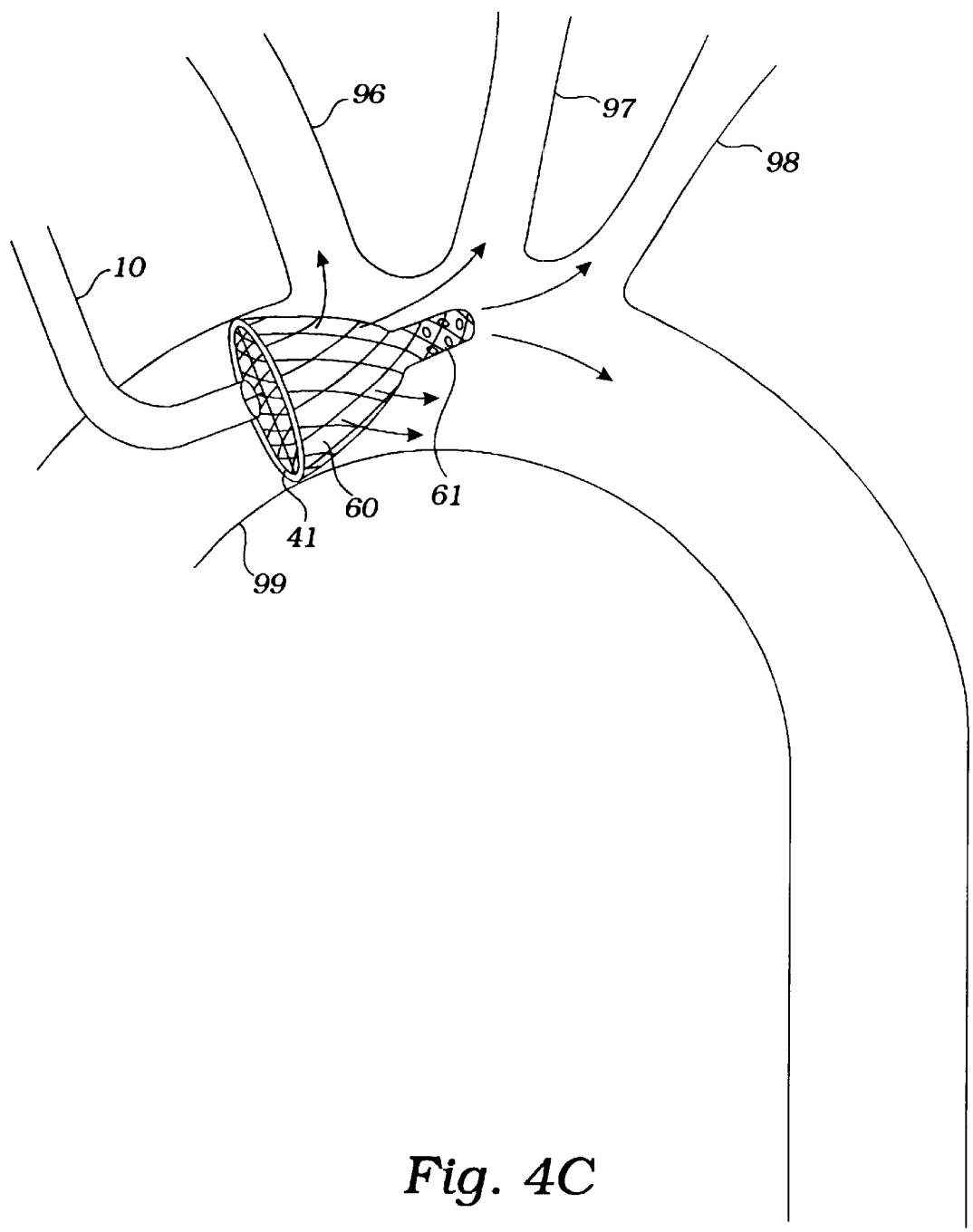
FIG. 4C depicts the use of the device of FIG. 4B in the ascending aorta.

FIG. 4C shows the use of a filter with reservoir tip in the ascending aorta. Expansion frame 41 is deployed through cannula 10 upstream the takeoff for right brachiocephalic artery 96, left common carotid artery 97, and left subclavian artery 98. Filter 60 includes reservoir tip 61. After filter 60 is deployed, arterial return is provided through cannula 10. After termination of arterial return flow, expansion frame 41 and filter 60 are removed through cannula 10 before removing cannula 10. These devices will find application in any surgeries that can make use of arterial cannulation and/or filter protection, including coronary artery bypass grafting, heart valve repair or replacement, septal defect repair, pulmonary thrombectomy, atherectomy, aneurysm repair, aortic dissection repair, and correction of congenital defects.

The length of the cannula will generally be between 15 and 60 centimeters, preferably approximately between 25 and 40 centimeters. The inner diameter of the cannula lumen will generally be between 0.5 and 1.5 centimeters, preferably between 0.5 and 1.0 centimeters. The diameter of the expanded filter will generally be between 0.3 and 3.0 centimeters, preferably approximately 2.0 and 2.5 centimeters for use in the aorta. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, the devices and methods of each embodiment can be combined with or used in any of the other embodiments.

What is claimed is:

1. A cannula, comprising:
   an elongate tubular member having a proximal end, a distal end, and a lumen therebetween; and
   a blast plate deployable from within the lumen of the elongate tubular member and retractable into the lumen of the elongate tubular member;
   wherein, during use, the distal end of the elongate tubular member is inserted into a vessel, the blast plate is deployed from the lumen of the elongate tubular member beyond the distal end of the elongate tubular member, and blood flow is passed through the lumen of the elongate tubular member and against the blast plate.

2. The cannula of claim 1, wherein the elongate tubular member is angled at its distal end.

3. The cannula of claim 1, further comprising a filter deployable from the distal end of the elongate tubular member.

4. The cannula of claim 1, wherein the lumen is divided into more than one passage.

5. The cannula of claim 1, further comprising an occlusion member deployable from the distal end of the elongate tubular member.

6. The cannula of claim 1, wherein the blast plate comprises a membrane mounted on a flexible wire ring.

7. The cannula of claim 6, wherein the membrane is semi-permeable.

8. The cannula of claim 7, wherein the membrane is a mesh.

9. The cannula of claim 6, wherein the membrane is impermeable.

10. The cannula of claim 1, wherein the blast plate is a cone-shaped sleeve.

11. The cannula of claim 10, wherein the sleeve is an elastomeric material.

12. The cannula of claim 1, wherein the blast plate comprises a substantially flat surface mounted at a distal end of a flexible elongate member.

13. The cannula of claim 12, wherein the flexible elongate member is a wire.

14. The cannula of claim 12, wherein the surface is attached to the flexible elongate member at substantially a 45° angle.

15. The cannula of claim 3, wherein the filter further comprises an embolic trap at its distal end.

16. The cannula of claim 15, wherein the embolic trap is a windsock.

17. A surgical method, comprising the steps of:
    inserting a cannula into a blood vessel, the cannula comprising an elongate tubular member having a proximal end, a distal end, and a lumen therebetween;
    advancing a blast plate from the lumen of the elongate tubular member beyond the distal end of the elongate tubular member;
    flowing a blood stream through the lumen of the elongate tubular member against the blast plate, wherein the blood stream is diffused by the blast plate; and
    retracting the blast plate into the lumen of the elongate tubular member.

18. The method of claim 17, wherein the blood vessel is an artery.

19. The method of claim 18, wherein the artery is the aorta.

20. The method of claim 17, wherein the elongate tubular member is angled at its distal end.

* * * * *